US012788533B2

(12) United States Patent
Kirsanov et al.

(10) Patent No.: US 12,788,533 B2
(45) Date of Patent: Nov. 10, 2026

(54) SYSTEMS AND METHODS FOR SETTING TOOTH AXIS

(71) Applicant: Align Technology, Inc., San Jose, CA (US)

(72) Inventors: Dmitry Kirsanov, Moscow (RU); Pavel Loginov, Morrisville, NC (US); Mikhail Gorodilov, Cary, NC (US); Georgiy Aloyan, Obninsk (RU); Vasily Paraketsov, Moscow (RU)

(73) Assignee: Align Technology, Inc., San Jose, CA (US)

( * ) Notice: Subject to any disclaimer, the term of this patent is extended or adjusted under 35 U.S.C. 154(b) by 61 days.

(21) Appl. No.: 18/595,395

(22) Filed: Mar. 4, 2024

(65) Prior Publication Data

US 2024/0293200 A1 Sep. 5, 2024

Related U.S. Application Data

(60) Provisional application No. 63/488,470, filed on Mar. 3, 2023.

(51) Int. Cl.
*A61C 7/00* (2006.01)
*A61C 9/00* (2006.01)
*A61C 13/34* (2006.01)
*G16H 50/50* (2018.01)

(52) U.S. Cl.
CPC ............ *A61C 7/002* (2013.01); *A61C 9/0053* (2013.01); *A61C 13/34* (2013.01); *G16H 50/50* (2018.01); *A61C 2007/004* (2013.01)

(58) Field of Classification Search
CPC ....... A61C 7/002; A61C 9/0053; A61C 13/34; A61C 2007/004; G16H 50/50
USPC .......................................................... 433/24
See application file for complete search history.

(56) References Cited

U.S. PATENT DOCUMENTS

| | | | |
|---|---|---|---|
| 5,975,893 | A | 11/1999 | Chishti et al. |
| 6,227,850 | B1 | 5/2001 | Chishti et al. |
| 6,227,851 | B1 | 5/2001 | Chishti et al. |
| 6,299,440 | B1 | 10/2001 | Phan et al. |
| 6,318,994 | B1 | 11/2001 | Chishti et al. |
| 6,371,761 | B1 | 4/2002 | Cheang et al. |
| 6,386,878 | B1 | 5/2002 | Pavlovskaia et al. |
| 6,406,292 | B1 | 6/2002 | Chishti et al. |
| 6,409,504 | B1 | 6/2002 | Jones et al. |
| 6,457,972 | B1 | 10/2002 | Chishti et al. |
| 6,488,499 | B1 | 12/2002 | Miller |
| 6,514,074 | B1 | 2/2003 | Chishti et al. |
| 6,554,611 | B2 | 4/2003 | Chishti et al. |
| 6,582,229 | B1 | 6/2003 | Miller et al. |
| 6,602,070 | B2 | 8/2003 | Miller et al. |
| 6,621,491 | B1 | 9/2003 | Baumrind et al. |
| 6,688,886 | B2 | 2/2004 | Hughes et al. |
| 6,726,478 | B1 | 4/2004 | Isiderio et al. |
| 6,729,876 | B2 | 5/2004 | Chishti et al. |
| 6,739,869 | B1 | 5/2004 | Taub et al. |
| 6,767,208 | B2 | 7/2004 | Kaza |

(Continued)

*Primary Examiner* — Matthew M Nelson
(74) *Attorney, Agent, or Firm* — Shay Glenn LLP

(57) ABSTRACT

Apparatuses (e.g., systems) and methods for quickly and accurately determining tooth axis information associated with a subject's dental data. A stage of a prior treatment plan that most closely matches to a digital model of a subject's current dentition may be used to approximate tooth axis information for the subject's current dentition.

24 Claims, 6 Drawing Sheets

(56) References Cited

U.S. PATENT DOCUMENTS 6,783,360 B2 8/2004 Chishti
7,040,896 B2 5/2006 Pavlovskaia et al.
7,063,532 B1 6/2006 Jones et al.
7,074,038 B1 7/2006 Miller
7,074,039 B2 7/2006 Kopelman et al.
7,077,647 B2 7/2006 Choi et al.
7,108,508 B2 9/2006 Hedge et al.
7,134,874 B2 11/2006 Chishti et al.
7,156,661 B2 1/2007 Choi et al.
7,160,107 B2 1/2007 Kopelman et al.
7,241,142 B2 7/2007 Abolfathi et al.
7,293,988 B2 11/2007 Wen
7,309,230 B2 12/2007 Wen
7,357,634 B2 4/2008 Knopp
7,555,403 B2 6/2009 Kopelman et al.
7,637,740 B2 12/2009 Knopp
7,689,398 B2 3/2010 Cheng et al.
7,736,147 B2 6/2010 Kaza et al.
7,746,339 B2 6/2010 Matov et al.
7,844,356 B2 11/2010 Matov et al.
7,844,429 B2 11/2010 Matov et al.
7,865,259 B2 1/2011 Kuo et al.
7,878,804 B2 2/2011 Korytov et al.
7,880,751 B2 2/2011 Kuo et al.
7,904,308 B2 3/2011 Arnone et al.
7,930,189 B2 4/2011 Kuo
7,942,672 B2 5/2011 Kuo
7,970,627 B2 6/2011 Kuo et al.
7,970,628 B2 6/2011 Kuo et al.
8,038,444 B2 10/2011 Kitching et al.
8,044,954 B2 10/2011 Kitching et al.
8,075,306 B2 12/2011 Kitching et al.
8,092,215 B2 1/2012 Stone-Collonge et al.
8,099,268 B2 1/2012 Kitching et al.
8,108,189 B2 1/2012 Chelnokov et al.
8,126,726 B2 2/2012 Matov et al.
8,260,591 B2 9/2012 Kass et al.
8,275,180 B2 9/2012 Kuo
8,401,826 B2 3/2013 Cheng et al.
8,439,672 B2 5/2013 Matov et al.
8,562,338 B2 10/2013 Kitching et al.
8,591,225 B2 11/2013 Wu et al.
8,788,285 B2 7/2014 Kuo
8,843,381 B2 9/2014 Kuo et al.
8,874,452 B2 10/2014 Kuo
8,896,592 B2 11/2014 Boltunov et al.
8,930,219 B2 1/2015 Trosien et al.
9,037,439 B2 5/2015 Kuo et al.
9,060,829 B2 6/2015 Sterental et al.
9,125,709 B2 9/2015 Matty
9,211,166 B2 12/2015 Kuo et al.
9,220,580 B2 12/2015 Borovinskih et al.
9,364,296 B2 6/2016 Kuo
9,375,300 B2 6/2016 Matov et al.
9,414,897 B2 8/2016 Wu et al.
9,492,245 B2 11/2016 Sherwood et al.
9,642,678 B2 5/2017 Kuo
10,248,883 B2 4/2019 Borovinskih et al.
10,342,638 B2 7/2019 Kitching et al.
10,463,452 B2 11/2019 Matov et al.
10,595,966 B2 3/2020 Carrier, Jr. et al.
10,617,489 B2 4/2020 Grove et al.
10,722,328 B2 7/2020 Velazquez et al.
10,758,322 B2 9/2020 Pokotilov et al.
10,779,718 B2 9/2020 Meyer et al.
10,792,127 B2 10/2020 Kopelman et al.
10,828,130 B2 11/2020 Pokotilov et al.
10,835,349 B2 11/2020 Cramer et al.
10,973,611 B2 4/2021 Pokotilov et al.
10,996,813 B2 5/2021 Makarenkova et al.
10,997,727 B2 5/2021 Xue et al.
11,020,205 B2 6/2021 Li et al.
11,020,206 B2 6/2021 Shi et al.
11,026,766 B2 6/2021 Chekh et al.
11,033,359 B2 6/2021 Velazquez et al.
11,071,608 B2 7/2021 Derakhshan et al.
11,096,763 B2 8/2021 Akopov et al.
11,116,605 B2 9/2021 Nyukhtikov et al.
11,147,652 B2 10/2021 Mason et al.
11,151,753 B2 10/2021 Gao et al.
11,154,381 B2 10/2021 Roschin et al.
11,241,301 B1 * 2/2022 Wucher ................. A61B 5/1111
11,259,896 B2 3/2022 Matov et al.
11,357,598 B2 6/2022 Cramer
11,395,717 B2 7/2022 Yuryev et al.
11,432,908 B2 9/2022 Kopelman et al.
11,464,604 B2 10/2022 Makarenkova et al.
11,478,334 B2 10/2022 Matov et al.
11,484,389 B2 11/2022 Sterental et al.
11,521,732 B2 12/2022 Levin et al.
11,534,272 B2 12/2022 Li et al.
11,553,988 B2 1/2023 Mednikov et al.
11,633,268 B2 4/2023 Moalem et al.
11,642,195 B2 5/2023 Gao et al.
11,651,494 B2 5/2023 Brown et al.
11,654,001 B2 5/2023 Roschin et al.
11,707,344 B2 7/2023 Roschin et al.
11,810,271 B2 11/2023 Shi et al.
11,850,111 B2 12/2023 Derakhshan et al.
2002/0010568 A1 * 1/2002 Rubbert ................. A61C 7/146 703/6
2002/0150859 A1 * 10/2002 Imgrund .................. A61C 7/00 433/24
2003/0008259 A1 1/2003 Kuo et al.
2003/0143509 A1 7/2003 Kopelman et al.
2003/0207227 A1 11/2003 Abolfathi
2004/0029068 A1 * 2/2004 Sachdeva ............... G16H 50/50 433/24
2004/0137400 A1 7/2004 Chishti et al.
2004/0152036 A1 8/2004 Abolfathi
2004/0197728 A1 10/2004 Abolfathi et al.
2004/0259049 A1 12/2004 Kopelman et al.
2005/0043837 A1 * 2/2005 Rubbert ................... A61C 7/00 700/118
2005/0182654 A1 8/2005 Abolfathi et al.
2005/0244791 A1 11/2005 Davis et al.
2006/0127836 A1 6/2006 Wen
2006/0127852 A1 6/2006 Wen
2006/0127854 A1 6/2006 Wen
2006/0275731 A1 12/2006 Wen et al.
2006/0275736 A1 12/2006 Wen et al.
2007/0168152 A1 * 7/2007 Matov .................... A61C 7/002 702/155
2008/0305451 A1 * 12/2008 Kitching .................. A61C 7/00 433/24
2008/0305453 A1 * 12/2008 Kitching .................. A61C 7/08 433/213
2008/0306724 A1 12/2008 Kitching et al.
2010/0009308 A1 1/2010 Wen et al.
2010/0068672 A1 3/2010 Arjomand et al.
2010/0068676 A1 3/2010 Mason et al.
2010/0092907 A1 4/2010 Knopp
2010/0167243 A1 7/2010 Spiridonov et al.
2013/0204599 A1 8/2013 Matov et al.
2014/0379356 A1 * 12/2014 Sachdeva ............... A61C 7/002 705/2
2017/0273760 A1 9/2017 Morton et al.
2018/0168781 A1 * 6/2018 Kopelman .............. G06T 17/00
2018/0206940 A1 * 7/2018 Kopelman ............ G06T 7/0012
2018/0280118 A1 10/2018 Cramer
2019/0192259 A1 * 6/2019 Kopelman ............. A61B 5/682
2019/0328487 A1 10/2019 Levin et al.
2019/0328488 A1 10/2019 Levin et al.
2020/0000554 A1 * 1/2020 Makarenkova ........ G16H 50/50
2020/0155274 A1 5/2020 Pimenov et al.
2020/0297458 A1 9/2020 Roschin et al.
2020/0306011 A1 * 10/2020 Chekhonin ............ G16H 30/40
2021/0134436 A1 5/2021 Meyer et al.
2022/0030162 A1 * 1/2022 Cramer ................ A61C 9/0053
2022/0079714 A1 * 3/2022 Paraketsov ............. G06T 7/251
2022/0165388 A1 5/2022 Chernov et al.
2024/0197449 A1 * 6/2024 Stroganov .............. G16H 50/50
2024/0261063 A1 * 8/2024 McGann ................ A61B 34/10

(56) References Cited

U.S. PATENT DOCUMENTS

| | | | | |
|---|---|---|---|---|
| 2024/0293200 | A1* | 9/2024 | Kirsanov | A61C 7/002 |
| 2024/0293201 | A1* | 9/2024 | Kirsanov | A61C 13/34 |
| 2025/0127591 | A1* | 4/2025 | Joo | G06N 20/00 |
| 2025/0186169 | A1* | 6/2025 | Cramer | G16H 20/30 |

* cited by examiner

SYSTEMS AND METHODS FOR SETTING TOOTH AXIS

CROSS REFERENCE TO RELATED APPLICATIONS

This patent claims priority to U.S. Provisional Patent Application No. 63/488,470, titled "SYSTEMS AND METHODS FOR TOOTH NUMBERING AND SETTING TOOTH AXIS," filed on Mar. 3, 2023, herein incorporated by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference.

BACKGROUND

Orthodontic procedures typically involve repositioning a subject's teeth to a desired arrangement in order to correct malocclusions and/or improve aesthetics. To achieve these objectives, orthodontic appliances such as braces, shell aligners, and the like can be applied to the subject's teeth by an orthodontic practitioner and/or by the subjects themselves. The appliance can be configured to exert force on one or more teeth in order to effect desired tooth movements according to a treatment plan.

Orthodontic aligners may include devices that are removable and/or replaceable over the teeth. Orthodontic aligners may be provided as part of an orthodontic treatment plan. In some orthodontic treatment plans involving removable and/or replaceable aligners, a subject may be provided plurality of orthodontic aligners over the course of treatment to make incremental position adjustments to the subject's teeth. An orthodontic aligner may have a polymeric trough with an inner cavity shaped to receive and resiliently reposition teeth from one tooth arrangement to a successive tooth arrangement. Orthodontic aligners may include "active" regions that impose repositioning forces on teeth and "passive" regions that retain teeth in their current state.

Some orthodontic aligners make use of a three-dimensional (3D) model of the subject's teeth for treatment planning and tracking. The 3D modeling process can include scanning the subject's teeth with an intraoral scanner, generating a 3D model from the scanned data, and segmenting the 3D model to identify individual teeth and/or other intraoral features such as gingiva. Segmentation of 3D models is a complex computational process which can include separating teeth anatomy from gingiva and removing extra material and distortions from the scan. The result of the segmentation significantly affects treatment quality, and poor segmentation results can cause aligner fit issues, pain, and other customer complaints.

Subject dental data, such as two-dimensional (2D) and 3D image, and scan data is used to generate the subject's 3D model. In addition, accurate tooth numbers and tooth axis information is used to determine the subject's dental treatment plan. Any inaccuracies in the subject's 3D model, the subject's tooth numbers, and the subject's tooth axes may result in poor treatment quality from the dental treatment plan.

SUMMARY OF THE DISCLOSURE

Implementations described herein address the need to provide accurate tooth axis information and tooth numbers that are associated with a subject's current dental data. In general, information from previous dental data (used to determine a previous dental treatment plan) is selectively imported into the subject's current dental data. Thus, described herein are methods and apparatuses (e.g., systems, including software, firmware, etc.) for setting the individual tooth axes and/or tooth numbering for one or more teeth of a digital model of a subject's current dentition based on a closely-matched treatment stage from a prior dental or orthodontic treatment for which tooth numbering and/or tooth axes were determined. Any of these methods and systems may include determining that the prior treatment stage is sufficiently closely matched so that the tooth numbering and/or tooth axes may be reliably translated from the prior treatment stage to the current dentition by aligning the jaw position in the digital model of the subject's current dentition and the jaw position of the digital model of the prior dentition, matching the tooth position from the digital model of the subject's current dentition to the tooth position in all (or a subset) of the tooth position from the digital model of each of the stages ("treatment stages") of the subject's prior detention. The subject's prior dentition corresponds to a previous dental or orthodontic treatment comprising a plurality of treatment stages.

To import tooth axis information, individual teeth are first matched between a subject's previous dental data and the subject's current dental data. The teeth matching may include matching tooth shapes between the dental data sets. In some examples, a jaw position may be used to align the teeth in the dental data sets, enabling more accurate teeth matching. After tooth matching, tooth axis information is identified for each tooth in the subject's previous dental data and then imported to the subject's current dental data. In some examples, the matched tooth may have moved in the current dental data, with respect to the previous dental data. The imported tooth axis information may be adjusted to accommodate tooth motion.

In a similar manner, to import tooth numbers to the subject's current dental data, individual teeth are matched between the subject's previous and current dental data. Tooth numbers may be determined for the current dental data and compared to tooth numbers used in the previous dental data. If the tooth numbers do not match, tooth numbers from the previous dental data may be imported (used) as the tooth numbers in the current dental data.

In general, example apparatuses (e.g., devices, systems, etc.) and/or methods described herein may receive a subject's first dental data set, receive the subject's second dental data set, and match teeth included in the first dental data set to teeth included the second dental data set. Methods described herein may further include identifying tooth axis information for each tooth in the first dental data set, and importing the tooth axis information from teeth in the first dental data set into respective teeth of the second dental data set.

In general, the first dental data set may be associated with an earlier time or time period with respect to the second dental data set. For example, the first dental data set may have been collected earlier than the second dental data set. In some cases, the first dental data set may be associated with an earlier dental treatment plan with respect to the second dental data set.

In some examples, matching teeth may be based, at least in part, on matching a jaw position in the first dental data set to a jaw position in the second dental data set. In other words, the jaw position may be used to help align dental structures (including teeth) between the first dental data set and the second dental data set.

In some other examples, matching teeth in the first dental data set and the second dental data set may be based on matching tooth positions in dental arches of the first dental data set and the second dental data set.

In some cases, the first dental data set and the second dental data set may include segmented tooth information identifying individual teeth. The segmented teeth may then be subsequently matched.

In general, tooth axis information for each tooth may include distinct tooth axis information for each individual tooth. In some cases, neighboring teeth may have different tooth axis data. Furthermore, a tooth in the second dental data set may have moved in some respects to the same tooth in the first dental data set. Therefore, the associated tooth axis may have also moved with respect to the same tooth in the first dental data set. In some examples, the tooth axis data may be adjusted for each tooth in the second dental data set. The adjustment may be used to accommodate for tooth movement. The adjustment may include determining a transformation of the tooth axis information based at least in part on a difference in tooth position between the first dental data set and the second dental data set.

In some implementations, matching teeth may include matching a tooth shape in the first dental data set to a tooth shape in the second dental data set. For example, if two tooth shapes match between the first dental data set and the second dental data set, then the two teeth may be the same tooth represented in both the first and second dental data sets.

In general, the first dental data set and the second dental data set may be based on a subject's two-dimensional and three-dimensional image information. In some examples, the first dental data set and the second dental data set are received from a dental scanning system.

In some examples, the tooth axis information may include at least one of a polar and cartesian axes.

In any of the methods described herein, any of the procedures may be performed on a remote server. For example, matching teeth as described herein, may be performed on a remote server.

Also described herein are non-transitory computer-readable storage media storing instructions that, when executed by one or more processors, cause the one or more processors to receive a first dental data set of a subject, receive a second dental data set of the subject, match teeth in the first dental data set to teeth in the second dental data set, identify tooth axis information for each tooth in the first dental data set, and import the tooth axis information from teeth in the first dental data set into respective teeth of the second dental data set.

Also described herein are methods that may include receiving a first dental data set of a subject, receiving a second dental data set of the subject, matching teeth in the first dental data set to teeth in the second dental data set, determining tooth numbers in the second dental data set, and correcting the tooth numbers in the second dental data set based a comparison of the tooth numbers in the first dental data set and the second dental data set.

In general, the first dental data set may include any feasible dental information. For example, the first dental data set may include tooth numbers. In some cases, the first dental data set may include tooth numbers for each of the subject's teeth.

In some examples, the dental data sets may be associated with different dental treatment plans of a subject. For example, the first dental data set may be associated with a first dental treatment plan and the second dental data set may be associated with a second dental treatment plan, the first dental treatment plan determined before the second dental treatment plan.

In general, correcting the tooth numbers in the second dental data set may include replacing specific tooth numbers in the second dental data set with tooth numbers from the first dental data set. For example, correcting tooth numbers may include comparing tooth numbers of matching teeth in the first dental data set and the second dental data set, identifying a tooth number of a matched tooth in the second dental data set that does not match a tooth number of the matched tooth in the first dental data set, and replacing the identified tooth number of the matched tooth in the second dental data set with the tooth number of the matched tooth in the first dental data set.

In general, there may be several different approaches for matching teeth. In some examples, matching teeth may include matching teeth in the first dental data set and the second dental data set based on matching tooth positions in a dental arch. In some other examples, matching teeth may be based at least in part on matching a jaw position in the first dental data set to a jaw position in the second dental data set. In still other examples, matching teeth may include matching a tooth shape in the first dental data set to a tooth shape in the second dental data set.

In some variations, the first dental data set and the second dental data set includes segmented tooth information identifying individual teeth. The segmented tooth information may include tooth numbers.

In general, the first dental data set and the second dental data set may be based on a subject's two-dimensional and three-dimensional image information. In addition (or in the alternative), the first dental data set and the second dental data set may be received from a dental scanning system.

Described herein is a non-transitory computer-readable storage medium storing instructions that, when executed by one or more processors, cause the one or more processors to receive a first dental data set of a subject, receive a second dental data set of the subject, match teeth in the first dental data set to teeth in the second dental data set, determine tooth numbers in the second dental data set, and correct the tooth numbers in the second dental data set based a comparison of the tooth numbers in the first dental data set and the second dental data set.

As mentioned, the methods and apparatuses described herein for setting the individual tooth axes and/or tooth numbering for one or more teeth of a digital model of a subject's current dentition may identify a closely-matched treatment stage from a prior dental or orthodontic treatment for which tooth numbering and/or tooth axes were previously determined. Because the prior treatment stage was part of a treatment plan, either completed or partially completed, the tooth position and tooth numbering may have been validated as part of the earlier process. Although the number, orientation and location (and in some cases, even the shape) of the subject's current teeth may have changed since the prior treatment, the methods and apparatuses described herein are configured to account for these changes. In particular, these methods and apparatuses may determine which of the prior stages of the treatment plan best match the subject's current tooth position by confirming that teeth are in corresponding positions (in some examples, independent of tooth type and/or shape), e.g., comparing the digital models to find a best-matching stage, and then matching tooth shapes between the current dentition and the best-matching stage to confirm that tooth shapes are within a predetermined (or user-adjustable) matching threshold.

For example, any of these methods and systems may include: identifying a best match of a digital model of a subject's current dentition to a digital model of the subject's prior dentition, wherein the prior dentition corresponds to a previous dental or orthodontic treatment comprising a plurality of treatment stages, wherein identifying the best match comprises: matching a plurality of teeth positions of the subject's current dentition for the plurality of treatment stages to determine a best matching treatment stage of the plurality of treatment stages of the previous dental or orthodontic treatment; and importing the tooth axis information from the best matching treatment stage for teeth of the digital model of a subject's current dentition when deviations between tooth shapes of the subject's current dentition and tooth shapes of the best matching treatment stage are below a threshold.

In some examples, the method may include: receiving a digital model of a subject's current dentition; receiving a digital model of the subject's prior dentition, wherein the prior dentition corresponds to a previous dental or orthodontic treatment comprising a plurality of treatment stages; identifying a best match of the digital model of a subject's current dentition to the digital model of the subject's prior dentition, wherein identifying the best match comprises: matching a jaw position of the digital model of the subject's current dentition to a jaw position of the digital model of the subject's prior dentition; and matching a plurality of teeth positions of the subject's current dentition for the plurality of treatment stages to determine a best matching treatment stage of the plurality of treatment stages of the previous dental or orthodontic treatment; and importing the tooth axis information from the best matching treatment stage for teeth of the digital model of a subject's current dentition when deviations between tooth shapes of the subject's current dentition and tooth shapes of the best matching treatment stage are below a threshold; and outputting a revised digital model of the subject's current dentition for generating a new orthodontic treatment plan.

As mentioned above, in any of these methods and apparatuses the jaw positions may be adjusted initially. For example, any of these methods an apparatuses may include identifying the best match by matching a jaw position of the digital model of the subject's current dentition to a jaw position of the digital model of the subject's prior dentition prior to matching the plurality of teeth positions of the subject's current dentition for the plurality of treatment stages. The methods and apparatuses may include adjusting or translating (in the digital model or when comparing the digital model) the patient's current dentition so that the upper and/or lower jaws in the digital model of a subject's current dentition may be compared more directly with the digital model of each stage (treatment stage) of the prior treatment plan.

In some examples importing the tooth axis information from the best matching treatment stage may comprise setting a position of the tooth axis for individual teeth of the digital model of the subject's current dentition wherein the position of each tooth axis is transformed based on a comparison of the tooth shapes between the subject's current dentition and the best matching treatment stage.

Any of these methods and apparatuses may optionally include receiving the digital model of a subject's current dentition and/or receiving the digital model of the subject's prior dentition. The digital models may be received from the same source (e.g., a memory, a remote processor, etc.) or different locations. For example, the digital model of the subject's current dentition is received from an intraoral scanner. The digital models may be processed prior to performing the methods and apparatuses described herein. For example the digital model(s) may be segmented to identify individual teeth. In some examples the digital models may be scaled. For example, the digital model of a subject's current dentition may be segmented to identify individual teeth. Alternatively or additionally, the digital models may be transformed into similar reference frames (e.g., in some examples, as mentioned above, by adjusting the relative jaw positions, etc.) and/or similar formats. The tooth axis information may include at least one of a polar and cartesian axes.

In general, the tooth axis information for each tooth may include distinct tooth axis information for each individual tooth. The tooth axis information may include one or more axes (e.g., one axis, two axis, three axes, etc.).

The methods and apparatuses may generally output a revised digital model of the subject's current dentition. The revised digital model of the subject's current dentition may be configured for generating a new orthodontic treatment plan. For example, the revised digital model may include more accurate tooth number, individual tooth axes, etc. The revised digital model may be segmented. In some examples these methods and apparatuses may be part of a method or system for treatment planning; the methods and apparatuses may include outputting a new treatment plan. The new treatment plan may include plans for one or more (e.g., series) of dental appliances (e.g., aligners, retainers, palatal expanders, etc.) for treating the patient.

In some examples the methods and apparatuses described herein may provide output (display, generating a file for storage and/or display, etc.) indicating difference between the current dentition (e.g., tooth position and/or orientation, shape, tooth number, missing and/or new teeth, etc.).

Because of the computationally-intensive nature (and relative complexity) of the steps, the methods is typically performed electronically. The steps of the method may be performed locally (e.g., on a local processor) and/or remotely. For example, the step of matching teeth may be performed on a remote server.

Any of these methods and apparatuses may include setting tooth numbering for at least some of the teeth of the digital model of the subject's current dentition based on tooth number of teeth of the best matching treatment stage when deviations between tooth shapes of the subject's current dentition and tooth shapes of the best matching treatment stage are below a threshold.

For example, a method may include: identifying a best match of a digital model of a subject's current dentition to a digital model of the subject's prior dentition, wherein the prior dentition corresponds to a previous dental or orthodontic treatment comprising a plurality of treatment stages, wherein identifying the best match comprises: matching a plurality of teeth positions of the subject's current dentition for the plurality of treatment stages to determine a best matching treatment stage of the plurality of treatment stages of the previous dental or orthodontic treatment; and setting tooth numbering for at least some of the teeth of the digital model of the subject's current dentition based on tooth number of teeth of the best matching treatment stage when deviations between tooth shapes of the subject's current dentition and tooth shapes of the best matching treatment stage are below a threshold to form a revised digital model of the subject's current dentition.

For example, a method may include: receiving a digital model of a subject's current dentition; receiving a digital model of the subject's prior dentition, wherein the prior dentition corresponds to a previous dental or orthodontic treatment comprising a plurality of treatment stages; identifying a best match of the digital model of a subject's current dentition to the digital model of the subject's prior dentition, wherein identifying the best match comprises: matching a jaw position of the digital model of the subject's current dentition to a jaw position of the digital model of the subject's prior dentition; and matching a plurality of teeth positions of the subject's current dentition for the plurality of treatment stages to determine a best matching treatment stage of the plurality of treatment stages of the previous dental or orthodontic treatment; and setting tooth numbering for at least some of the teeth of the digital model of the subject's current dentition based on tooth number of teeth of the best matching treatment stage when deviations between tooth shapes of the subject's current dentition and tooth shapes of the best matching treatment stage are below a threshold to form a revised digital model of the subject's current dentition; and outputting the revised digital model of the subject's current dentition for generating a new orthodontic treatment plan.

Any of these methods and apparatuses may include both setting tooth axes and tooth numbering.

In any of these methods, setting tooth numbering may include correcting tooth numbering for at least some of the teeth of the digital model of the subject's current dentition.

As mentioned, above, identifying the best match may include matching a jaw position of the digital model of the subject's current dentition to a jaw position of the digital model of the subject's prior dentition prior to matching the plurality of teeth positions of the subject's current dentition for the plurality of treatment stages. Any of these methods may include receiving the digital model of a subject's current dentition and/or the digital model of the subject's prior dentition.

In general, these methods may include outputting the revised digital model of the subject's current dentition after setting tooth numbering, for generating a new orthodontic treatment plan.

In any of these methods and apparatuses, setting the tooth numbering may comprise: comparing tooth numbers of matching teeth in the digital model of the subject's current dentition and the best matching treatment stage; identifying a tooth number of a matched tooth in the digital model of the subject's current dentition that does not match a tooth number of the matched tooth in the best matching treatment stage; and replacing the identified tooth number of the matched tooth in the digital model of the subject's current dentition with the tooth number of the matched tooth in the best matching treatment stage.

Matching teeth in the best matching treatment stage and the digital model of the subject's current dentition may be based on matching tooth positions in a dental arch.

As mentioned above, also described herein is software, hardware and/or firmware for performing any of these methods described herein. For example, described herein are non-transitory computer-readable storage medium storing instructions that, when executed by one or more processors, cause the one or more processors to perform a method comprising: identifying a best match of a digital model of a subject's current dentition to a digital model of the subject's prior dentition, wherein the prior dentition corresponds to a previous dental or orthodontic treatment comprising a plurality of treatment stages, wherein identifying the best match comprises: matching a plurality of teeth positions of the subject's current dentition for the plurality of treatment stages to determine a best matching treatment stage of the plurality of treatment stages of the previous dental or orthodontic treatment; and importing the tooth axis information from the best matching treatment stage for teeth of the digital model of a subject's current dentition when deviations between tooth shapes of the subject's current dentition and tooth shapes of the best matching treatment stage are below a threshold; and outputting a revised digital model of the subject's current dentition for generating a new orthodontic treatment plan.

For example, described herein are non-transitory computer-readable storage medium storing instructions that, when executed by one or more processors, cause the one or more processors to perform a method comprising: identifying a best match of a digital model of a subject's current dentition to a digital model of the subject's prior dentition, wherein the prior dentition corresponds to a previous dental or orthodontic treatment comprising a plurality of treatment stages, wherein identifying the best match comprises: matching a plurality of teeth positions of the subject's current dentition for the plurality of treatment stages to determine a best matching treatment stage of the plurality of treatment stages of the previous dental or orthodontic treatment; and setting tooth numbering for at least some of the teeth of the digital model of the subject's current dentition based on tooth number of teeth of the best matching treatment stage when deviations between tooth shapes of the subject's current dentition and tooth shapes of the best matching treatment stage are below a threshold.

The methods and apparatuses described herein may be particularly helpful in reducing the time to generate new treatment plans in patients. In particular, these methods and apparatuses significantly reduce the time needed to process patients and prepare treatment plans and may allow for rapid and accurate generation of digital models of the patient's current teeth for generating orthodontic treatment plans.

All of the methods and apparatuses described herein, in any combination, are herein contemplated and can be used to achieve the benefits as described herein.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
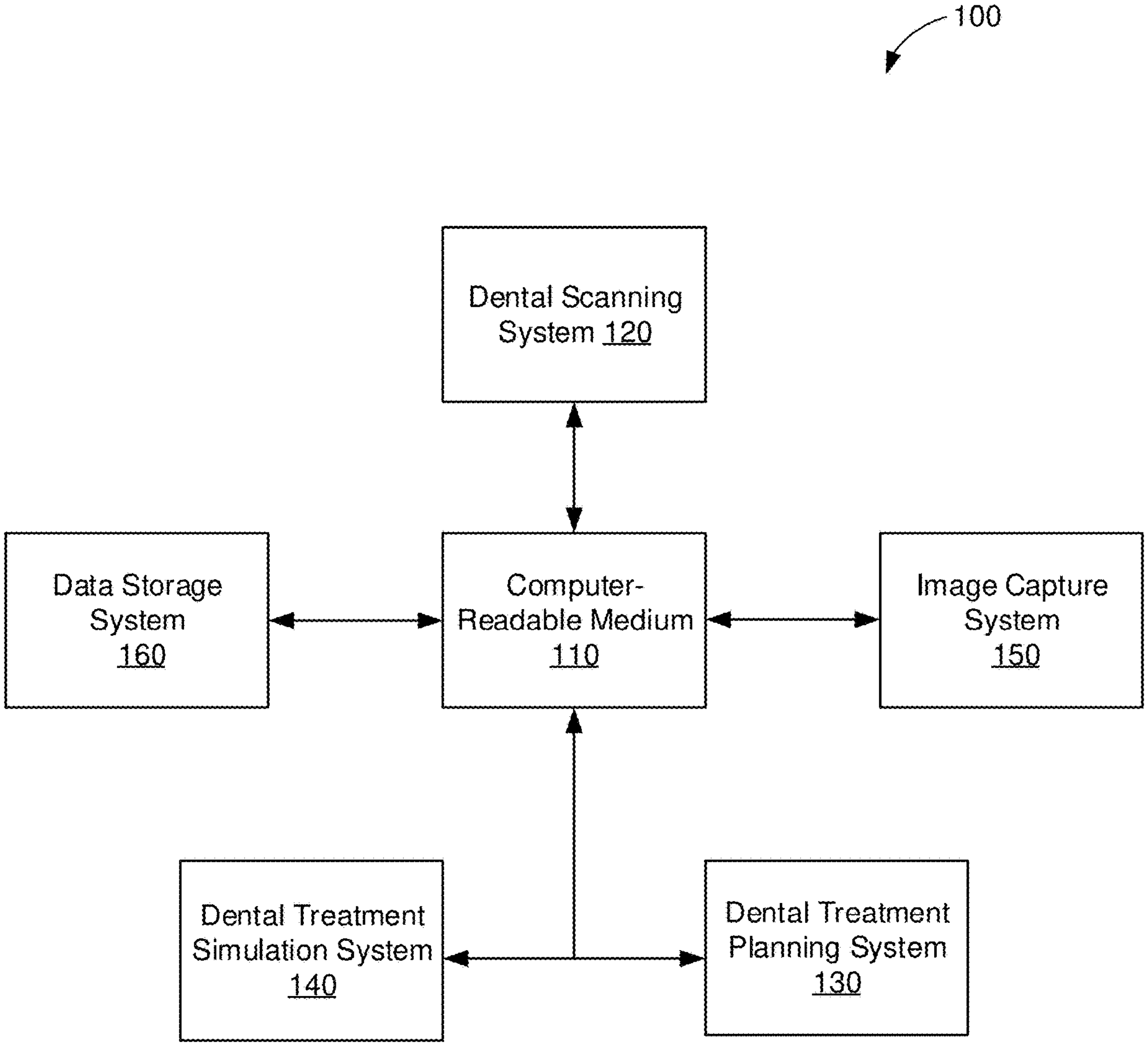
FIG. 1 shows a system for planning and simulating an orthodontic treatment.

Described herein are apparatuses (e.g., systems, computing device readable media, devices, etc.) and methods for improving the determination of tooth axes and tooth numbers. In some implementations, the apparatuses and methods described herein can use or import data from used to develop a subject's prior treatment plan to improve the data used to update the subject's current treatment plan. In particular, tooth axes and tooth number information may be imported from a subject's previous dental data (that may include images, scans, and the like) into a subject's current dental data. In some examples, the importation of information from the subject's previous dental data may be conditional. In some cases, the importation may be based on a detection or identification of an error condition with respect to the current dental data.

The apparatuses and/or methods described herein may be useful in planning and fabrication of dental appliances, including elastic polymeric positioning appliances, is described in detail in U.S. Pat. No. 5,975,893, and in published PCT application WO 98/58596, which is herein incorporated by reference for all purposes. Systems of dental appliances employing technology described in U.S. Pat. No. 5,975,893 are commercially available from Align Technology, Inc., San Jose, Calif., under the tradename, Invisalign System.

The terms "orthodontic aligner", "aligner", or "dental aligner" are synonymous with the terms "appliance" and "dental appliance" with regard to the dental applications described herein. For purposes of clarity, embodiments are hereinafter described within the context of the use and application of appliances, and more specifically "dental appliances."

A "subject," as used herein, may be any subject (e.g., human, non-human, adult, child, etc.) and may be alternatively and equivalently referred to herein as a "patient", a "patient under treatment", or a "subject." A "patient," as used herein, may but need not be a medical patient. An "subject" or a "patient," as used herein, may include a person who receives orthodontic treatment, including orthodontic treatment with a series of orthodontic aligners.

As described herein, any of a variety of tools can be used to convert a "real world" representation of a subject's dentition into a virtual model. For example, an image (e.g., picture or scan) of the dentition can be converted to a 2D or 3D model (e.g., 2D or 3D mesh). In some cases, a number of images are combined to create a single model. In some examples, an intraoral scanner generates multiple different images of a dental site, model of a dental site, or other object. The images may be discrete images (e.g., point-and-shoot images) or frames from a video (e.g., a continuous scan). The intraoral scanner may automatically generate a 3D model of the subject's teeth. In some cases, the 3D model includes the digital detailing and cut and detail processes during which a 3D mesh is converted into a CAD model with labeled teeth. A 3D dental mesh or model may include any feasible model, wireframe, and/or surface that describes or includes dimension information related to any feasible object or anatomy.

In a number of systems, a digital representation of a dental arch is partitioned into constituent parts, including teeth. This process is sometimes referred to segmentation or auto-segmentation. The teeth are then identified and numbered according to their dental tooth type. The tooth numbering may be used to create a treatment plan for correcting teeth locations. The process for both 2D images and 3D models or meshes generally begins by identifying which objects in the representation correspond to the central incisors and then working distally to identify the tooth number corresponding to the other objects. This process may cause errors in numbering if there are missing teeth and/or supernumerary teeth. For example, if a subject is missing their first premolars, then the system may mislabel the second premolars as first premolars and the first molars as second premolars. This is particularly likely when the subject's teeth differ from the norm. Thus during segmentation or auto-segmentation marked, the 2D images or 3D models/meshes may be labeled, divided, etc., to indicate different regions of the dentition, including individual teeth or regions of teeth (e.g., crown, root, etc.), gingiva, non-tooth regions (e.g., brackets, attachments, etc.). In some cases, regions or teeth may be labeled on the 3D models/meshes or in a separate index (e.g., file, database, etc.) referencing the 3D model/mesh. Some examples may divide the 2D images or 3D models into different sub-models. Auto-segmentation may refer to 3D models that are segmented using an automatic segmentation engine (e.g., module, subsystem, etc.) such as that described in detail in U.S. patent application Ser. No. 17/534,420, and in published PCT application WO 2022/109500, which is herein incorporated by reference for all purposes.

In some examples, the segmented or numbered teeth may include one or more tooth characteristics including a tooth shape. The shape of a tooth may be described by a two-dimensional or three-dimensional outline of the tooth. In some cases, the tooth shape may be used to identify any particular tooth due to the relatively distinct characteristics associated with any one tooth.

FIG. 1 shows an apparatus (e.g., a system) 100 for planning and/or simulating an orthodontic treatment. In the example of FIG. 1, the system 100 includes a computer-readable medium 110, a dental scanning system 120, a dental treatment planning system 130, a dental treatment simulation system 140, an image capture system 150, and a data storage system 160. One or more elements of system 100 may include computer readable media. The computer readable media may include instructions that, when executed by a processor (for example, a processor of any of systems 120, 130, 140, and 150) cause the respective system or systems to perform the processes described herein.

Dental scanning system 120 may include a computer system configured to capture one or more scans of a subject's dentition. Dental scanning system 120 may include a scan engine for capturing 2D or 3D images of a subject. Such images may include images of the subject's teeth, face, and jaw, for example. The images may also include x-rays, computed tomography, magnetic resonance imaging (MRI), cone beam computed tomography (CBCT), cephalogram images, panoramic x-ray images, digital imaging, and communication in medicine (DICOM) images, or other subsurface images of the subject. The scan engine may also capture 3D data representing the subject's teeth, face, gingiva, or other aspects of the subject.

Dental scanning system 120 may also include a 2D imaging system, such as a still or video camera, an x-ray machine, or other 2D imager. In some embodiments, dental scanning system 120 may also include a 3D imager, such as an intraoral scanner, an impression scanner, a tomography system, a cone beam computed tomography (CBCT) system, or other system as described herein, for example. The dental scanning system 120 and associated engines and imagers can be used to capture the 2D and 3D images of a subject's face and dentition for use in building a 3D parametric model of the subject's teeth as described herein. In some embodiments, the dental scanning system 120 may include systems, modules, and/or engines for segmenting dental scan data into portions of a subject's dentition including bones, gingiva, and/or teeth. Examples of parametric models of the subject's teeth suitable for incorporation in accordance with the present disclosure are describe in U.S. application Ser. No. 16/400,980, filed on May 1, 2019, entitled "Providing a simulated outcome of dental treatment on a subject", published as US20200000551 on Jan. 2, 2020, the entire disclosure of which is incorporated herein by reference.

Dental treatment simulation system 140 may include a computer system configured to simulate one or more estimated and/or intended outcomes of a dental treatment plan. In some implementations, dental treatment simulation system 140 obtains photos and/or other 2D images of a consumer/subject. Dental treatment simulation system 140 may further be configured to determine tooth, lip, gingiva, and/or other edges related to teeth in the 2D image. As noted herein, dental treatment simulation system 140 may be configured to match tooth and/or arch parameters to tooth, lip, gingiva, and/or other edges. Dental treatment simulation system 140 may also render a 3D tooth model of the subject's teeth. Dental treatment simulation system 140 may gather information related to historical and/or idealized arches representing an estimated outcome of treatment. Dental treatment simulation system 140 may, in various implementations, insert, align, etc. the 3D tooth model with the 2D image of the subject in order to render a 2D simulation of an estimated outcome of orthodontic treatment. Dental treatment simulation system 140 may include a photo parameterization engine which may further include an edge analysis engine, a course tooth alignment engine, and a 3D parameterization conversion engine. The dental treatment simulation system 140 may also include a parametric treatment prediction engine which may further include a treatment parameterization engine, a scanned tooth normalization engine, and a treatment plan remodeling engine. Dental treatment simulation system 140 and its associated engines may carry out the processes described herein.

Dental treatment planning system 130 may include a computer system configured to implement treatment plans. Dental treatment planning system 130 may include a rendering engine and interface for visualizing or otherwise displaying the simulated outcome of the dental treatment plan. For example, the rendering engine may render the visualizations of the 3D models described herein. Dental treatment planning system 130 may also determine an orthodontic treatment plan for moving a subject's teeth from an initial position, for example, based in part on the 2D image of the subject's teeth, to a final position. Dental treatment planning system 130 may be operative to provide for image viewing and manipulation such that rendered images may be scrollable, pivotable, zoomable, and interactive. Dental treatment planning system 130 may include graphics rendering hardware, one or more displays, and one or more input devices.

Some or all of dental treatment planning system 130 may be implemented on a personal computing device such as a desktop computing device or a handheld device, such as a mobile phone. In some embodiments, at least a portion of dental treatment planning system 130 may be implemented on a scanning system, such as dental scanning system 120. Image capture system 150 may include a device configured to obtain an image, including an image of a subject. The image capture system may comprise any type of mobile device (iOS devices, iPhones, iPads, iPods, etc., Android devices, portable devices, tablets), PCs, cameras (DSLR cameras, film cameras, video cameras, still cameras, etc.). In some implementations, image capture system 150 comprises a set of stored images, such as images stored on a storage device, a network location, a social media website, etc.

Some or all of the dental treatment planning system 130 may generate aligner data from which one or more orthodontic aligners may be fabricated. In this manner, the orthodontic aligners may be used to implement a dental treatment plan for a subject.

The data storage system 160 may be any device, system, or apparatus that provides temporary and/or persistent data storage. Examples of a data storage system 160 may include random access memory (RAM), dynamic random access memory (DRAM), solid state memory, disc-based memory, or the like. The data storage system 160 may store subject images, scan data, treatment plans, or any other feasible dental data. In some cases, scan data may include segmented tooth data, including tooth numbers and tooth axis data.

Any of these apparatuses may be configured to determine, using a prior treatment plan for the same patient, one or both of tooth axis information and/or tooth number information for all or some of the subject's teeth in a digital model of the subject's teeth. The digital model of the subject's teeth may be referred to as a "current" digital model or as a "first" digital model. The digital model may be a more taken more recently than the prior treatment plan.

Figure 2:
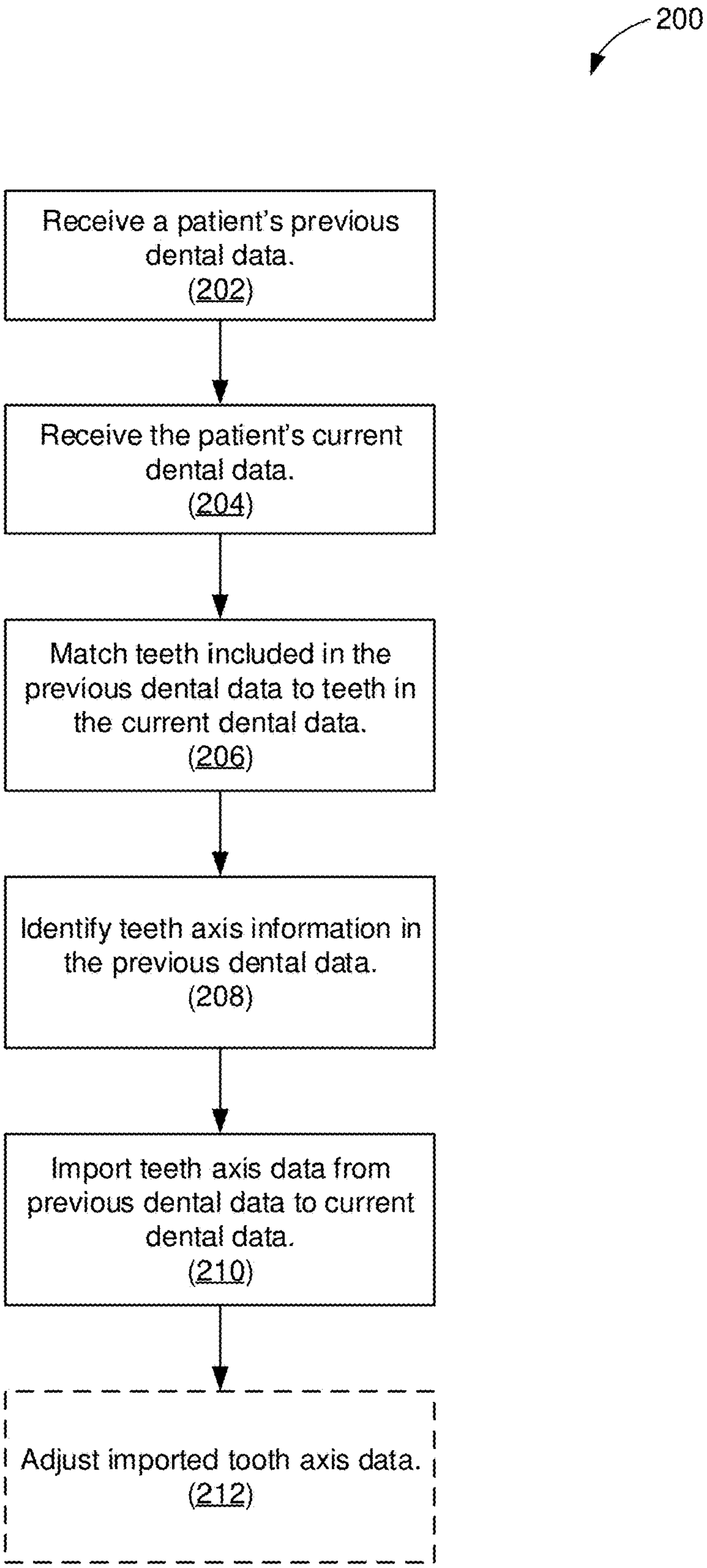
FIG. 2 is a flowchart showing an example method for determining tooth axes of a subject's teeth.

FIG. 2 is a flowchart showing an example method 200 for determining tooth axes of a subject's teeth. Some examples may perform the operations described herein with additional operations, fewer operations, operations in a different order, operations in parallel, and some operations differently. The method 200 is described below with respect to the system 100 of FIG. 1, however, the method 200 may be performed by any other suitable system or device.

The method 200 begins in block 202 as the system 100 receives or obtains a subject's prior dental data. Dental data may sometimes be referred to as a dental data set. Prior dental data may include a treatment plan including multiple stages reflecting incremental tooth movement. The prior dental data corresponds to a previous dental or orthodontic treatment plan. Example subject dental data includes dental scan data, segmentation data (data used to identify individual teeth), tooth data (tooth numbering and/or tooth axis data) as well as any other feasible data. As mentioned, previous dental data may be associated with a previously determined dental treatment plan and/or previous dental treatment. In some examples, the previous dental data may include 2D and/or 3D image information of the subject, including the subject's dentition as well as any feasible surrounding area such as subject bone structure including the subject's jaw.

For example, a subject may have been previously scanned thereby generating previous dental data. The previous dental data may then have been used to generate a related previous dental treatment plan. One or more dental aligners may have been developed in accordance with the dental treatment plan. Determination of the dental treatment plan may have included the determination of tooth axis data and/or tooth numbering. Thus, tooth axis data and tooth numbering may be included with the previous dental data.

In general, dental scan data may have been captured by the image capture system 150 or the dental scanning system 120. For example, the 2D and 3D image information may be provided by or received from the dental scanning system 120 and/or the image capture system 150. The previous dental data may be stored in the data storage system 160.

Next, in block 204, the system 100 receives and/or obtains a subject's current dental data. In some cases, the dental scanning system 120 and/or the image capture system 150 may capture or generate current dental data which may include current dental scan data. The dental scan data may include 2D and/or 3D image information of the subject, including the subject's dentition as well as any feasible surrounding area such as subject bone structure including the subject's jaw.

In some examples, the dental scanning system 120 may process the dental scan data to determine a subject's bone structure, gingiva, teeth, dental arch, or other portions of the subject's dentition. In some variations, the dental scanning system 120 also may segment some or all of the dental scan data to determine the subject's individual teeth.

The current dental data may be similar to the subject's previous dental data collected or captured during a previous time period. For example, the previous dental data may have been collected or captured before or prior to the current dental data.

Next, in block 206 the system 100 matches teeth included in the previous dental data to teeth in the current dental data (the subject's current dentition). A correspondence between teeth may indicate a match between identical teeth within the two different dental data sets. For example, the system 100 may determine that a tooth number 5 in the previous dental data has a correspondence with tooth number 5 in the current dental data. In this manner, the system 100 can match teeth between the different dental data sets.

Correspondence (matches) between teeth may be determined in a variety of ways. For example, the system 100 may align scan data of the previous dental data with scan data included current dental data, using a jaw to guide alignment between the data sets. The jaw position in the previous dental data may be used with the jaw position in the current dental data to assist in determining teeth correspondence.

In some other examples, the system 100 may use determined tooth positions in the previous dental data and the current dental data to determine tooth correspondence. For example, the system 100 may match a tooth position on a dental arch of described within the previous dental data to a tooth position in a dental arch described within of the current dental data.

In some variations, the system 100 may use tooth shape to determine tooth correspondence. For example, the system 100 may match a tooth shape in the previous dental data with a tooth shape in the current dental data. The tooth shape may include ridges, grooves, cusps, other outward or external physical tooth characteristics. A subject's tooth shape does not change substantially over time, and thus can be a good indicator or marker with which to match a subject's teeth.

In some examples, the correspondence between teeth may be based on a comparison of a metric within a threshold. For example, the system 100 may compare the shape of a first tooth in the previous dental data to the shape of a first tooth in the current dental data. If the shape of the first tooth in the previous dental data is within a threshold measurement of the shape of the first tooth in the current dental data, then the system 100 may have found or matched corresponding teeth. The threshold measurement may be any feasible measurement (tooth shape, tooth length, tooth rotation, and the like).

The matching performed by the system 100 in block 206 may be performed with any feasible processor, compute node, of the like. In some examples, operations associated with block 206 may be performed by a compute device (remove server, processor, state machine, etc.) that is coupled to the system 100 with any feasible network.

Next, in block 208 the system 100 identifies tooth axis data for each tooth in the previous dental data. As described above, the previous dental data may include tooth axis data that was determined for each tooth when a previous dental treatment was developed. Generally, the tooth axis data for each tooth may be unique for each tooth. Thus, tooth axis data for a first tooth may be different from tooth axis data for a second tooth.

Tooth axis data may include any coordinate system that describes a position and/or orientation of any tooth. Tooth axis data may also describe or locate an origin of a tooth. Any feasible coordinate system may be used to describe tooth axis. In some examples, the tooth axis information may include cartesian (x, y, and z) and/or a polar (r, θ, and φ) coordinate systems.

Next, in block 210, the system 100 imports the tooth axis data from the previous dental data into the current dental data. Importing the tooth axis data may reduce errors in determining tooth axis data and may speed up any following procedures including determining a new dental treatment plan. In some examples, the system 100 may import or use tooth axis data (from the previous dental data) instead of analyzing the current dental data to determine new tooth axis data.

Next, in block 212 the system 100 can optionally adjust the imported tooth axis data. (The optional nature is illustrated with dashed lines in FIG. 2). In some cases, a particular tooth in the current dental data may have moved or otherwise have been displaced from an initial position in the previous dental data. In some cases, the system 100 may adjust the imported tooth axis information to accommodate for any tooth displacement. For example, the system 100 may determine a transformation function that associates an initial tooth position in the previous dental data with a corresponding tooth position in the current dental data. The transformation function may then be used to transform the imported tooth axis data in a manner consistent with the determined tooth movement. In some variations, the transformation function may be determined, at least in part, by finding a best fit function that correlates the initial tooth position with the current tooth position as identified by tooth shape. In some examples, the transformation function may be a three-dimensional transformation function.

Figure 3:
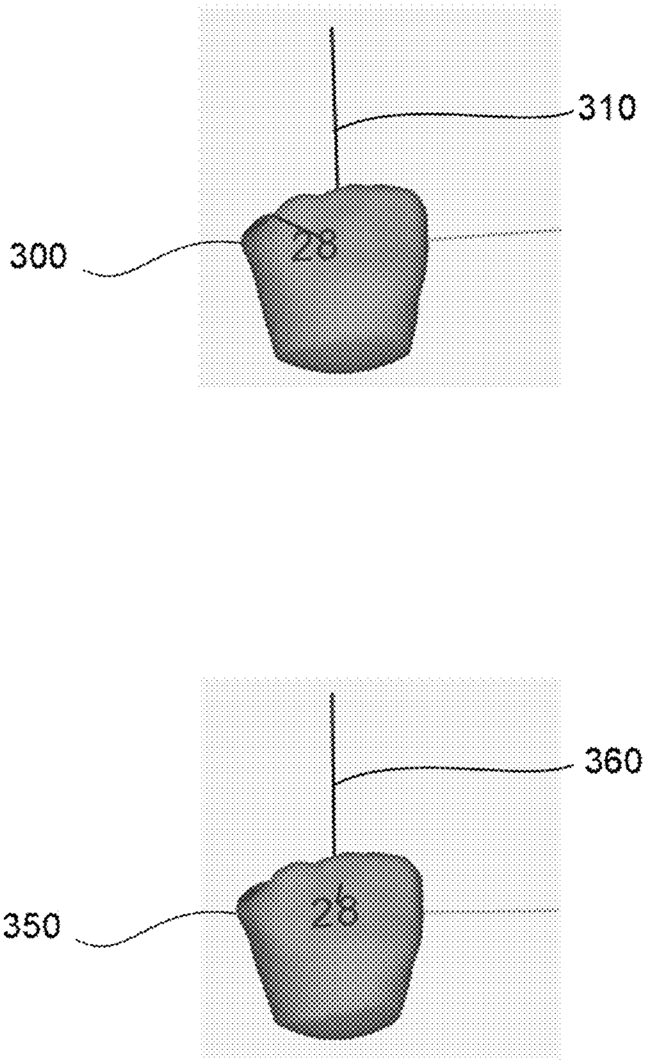
FIG. 3 shows example teeth and their related tooth axis data.

FIG. 3 shows example teeth and their related tooth axis data. Tooth 300 is a tooth associated with previous dental data. The tooth 300 may include tooth axis data 310 (shown here as x, y, and z axes, but other tooth axes are possible and not shown here. For example, instead of the tooth axis data 310 having x, y, z (e.g., Cartesian) axes, the tooth axis data 310 may have polar axes or any other feasible tooth axes.

Tooth 350 is a tooth associated with current dental data. Tooth axis data 360 may be imported from the previous dental data into the current dental data and related to the tooth 350. In some cases, the position of tooth 350 may be slightly different with respect to the position of the corresponding tooth in the previous dental data. In some cases, the system 100 of FIG. 1 may adjust (transform, rotate, and the like) the tooth axis 360 to accommodate any tooth displacement of tooth 350 with respect to tooth 300.

Figure 4:
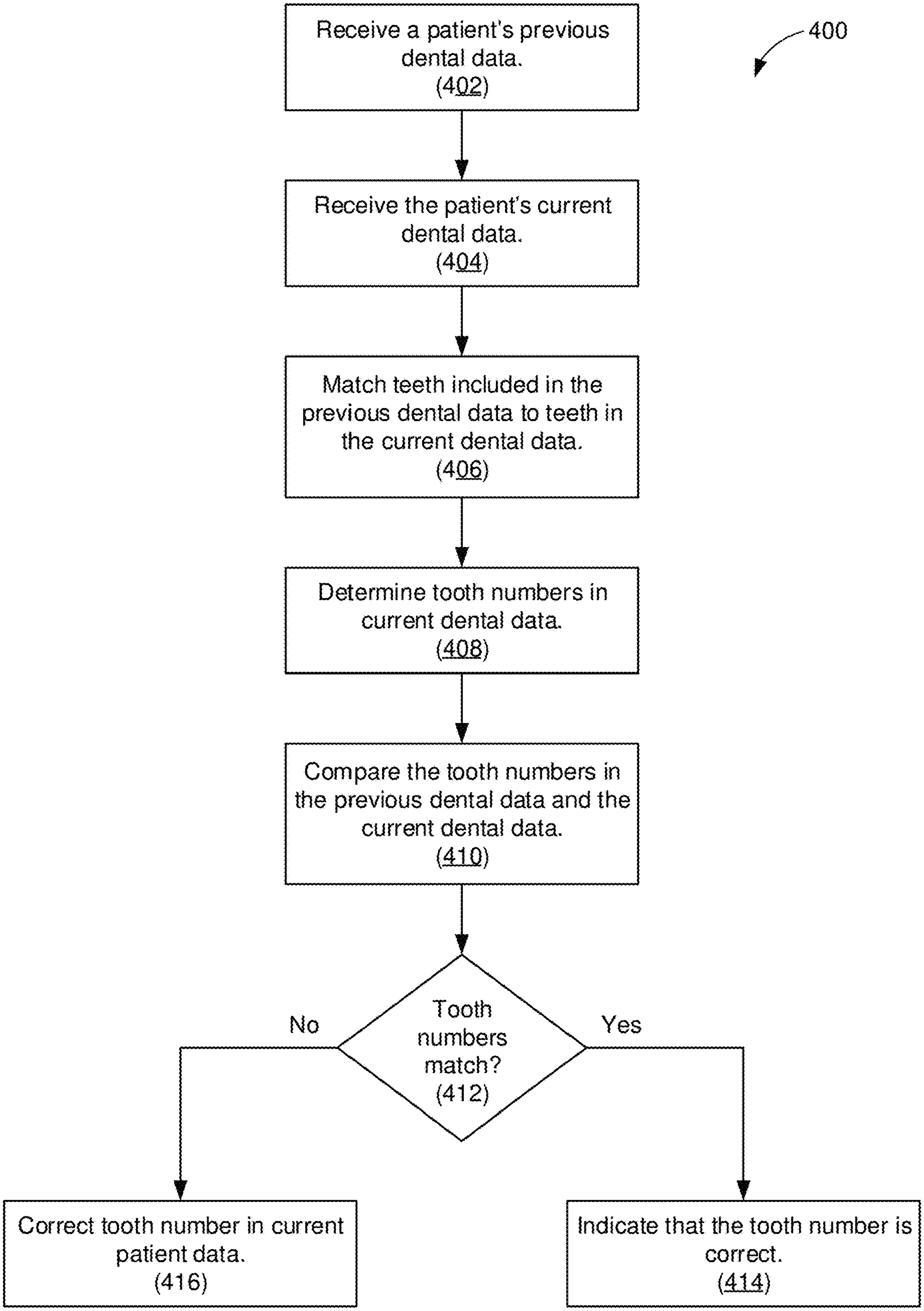
FIG. 4 is a flowchart showing an example method for determining the tooth numbering of a subject's teeth.

FIG. 4 is a flowchart showing an example method 400 for determining the tooth numbering of a subject's teeth. The method 200 is described below with respect to the system 100 of FIG. 1, however, the method 200 may be performed by any other suitable system or device.

The method 400 begins in block 402 as the system 100 receives and/or obtains a subject's previous dental data. Next, in block 404 the system 100 obtains and/or receives a subject's current dental data. And next, in block 406, the system 100 matches teeth included in the previous dental data to teeth in the current dental data. Operations of the blocks 402, 404, and 406 correspond to operations of the blocks 202, 204, and 206 described in FIG. 2. Thus, an explanation of the operations of the blocks 402, 404, and 406 is not repeated here.

Next, in block 408 the system 100 determines the tooth numbers of teeth in the current dental data. For example, the system 100 can segment teeth included in the current dental data and determine the tooth numbers associated with each segmented tooth. In some cases, the determined tooth numbers associated with the current dental data may include unintentional errors. That is, the system 100 may have incorrectly determined some tooth numbers of teeth in the current dental data.

Next, in block 410 the system compares the tooth numbers of each tooth in the previous dental data and the corresponding tooth in the current dental data. If the tooth numbers match (as checked in block 412), then in block 414, the system 100 indicates or marks that the tooth number of the corresponding (e.g., matching) tooth is correct. On the other hand, if the tooth numbers do not match, then in block 416 the system 100 corrects the tooth number in the current dental data.

In some examples, the previous order of teeth (e.g., tooth number order in the previous dental data) may be used to provide guidance in determining the correct tooth number. Recall that previous dental data may have been used to determine a dental treatment plan, and thus the previous tooth numbers may have already been reviewed and accepted by a clinician or other dental service provider.

In some cases, the system 100 may determine that no teeth have been extracted between the time that the previous dental data was collected and the time that the current dental data was collected. In such cases, previous tooth numbers may be used to correct errors in the current dental data. Table 1 below shows corrected (imported) tooth numbers based on previous tooth number data. The corrected tooth numbers are shown in bold face type in Table 1.

TABLE 1

| Tooth Numbers (previous) | Tooth Numbers (current) | Imported Tooth Numbers |
|---|---|---|
| 5, 7, 8 | 5, 6, 8 | 5, 7, 8 |
| 5, 6, 8 | 5, 7, 8 | 5, 6, 8 |
| 5, 6, 9 | 5, 8, 9 | 5, 6, 9 |

In some examples, the system 100 may use similar teeth positions and tooth numbers to determine the tooth numbers in the current dental data. Teeth extractions, particularly those that may have occurred after the time that the previous dental data was collected may adversely affect the tooth numbers determined in block 408. Again, previously determined tooth numbers (associated with the previous dental data) may offer guidance in determining the imported tooth numbers. Table 2 below shows example changes that the system 100 may perform to determine corrected (imported) tooth numbers. The corrected tooth numbers are shown in bold face type in Table 2.

TABLE 2

| Tooth Numbers (previous) | Tooth Numbers (current) | Imported Tooth Numbers |
|---|---|---|
| 5, 7, 8 | 5, 6, 8 | 5, 7, 8 |
| 5, 7, 9, 10 | 5, 6, 8, 10 | 5, 7, 9, 10 |
| 5, 6, 9 | 5, 7, 8, 9 | 5, 7, 8, 9 (no correction made) |

In some cases, the information included in the tooth numbers from the previous dental data and the tooth numbers from the current dental data are not sufficient to make a correction. This is illustrated in the last line of Table 2.

Figure 5:
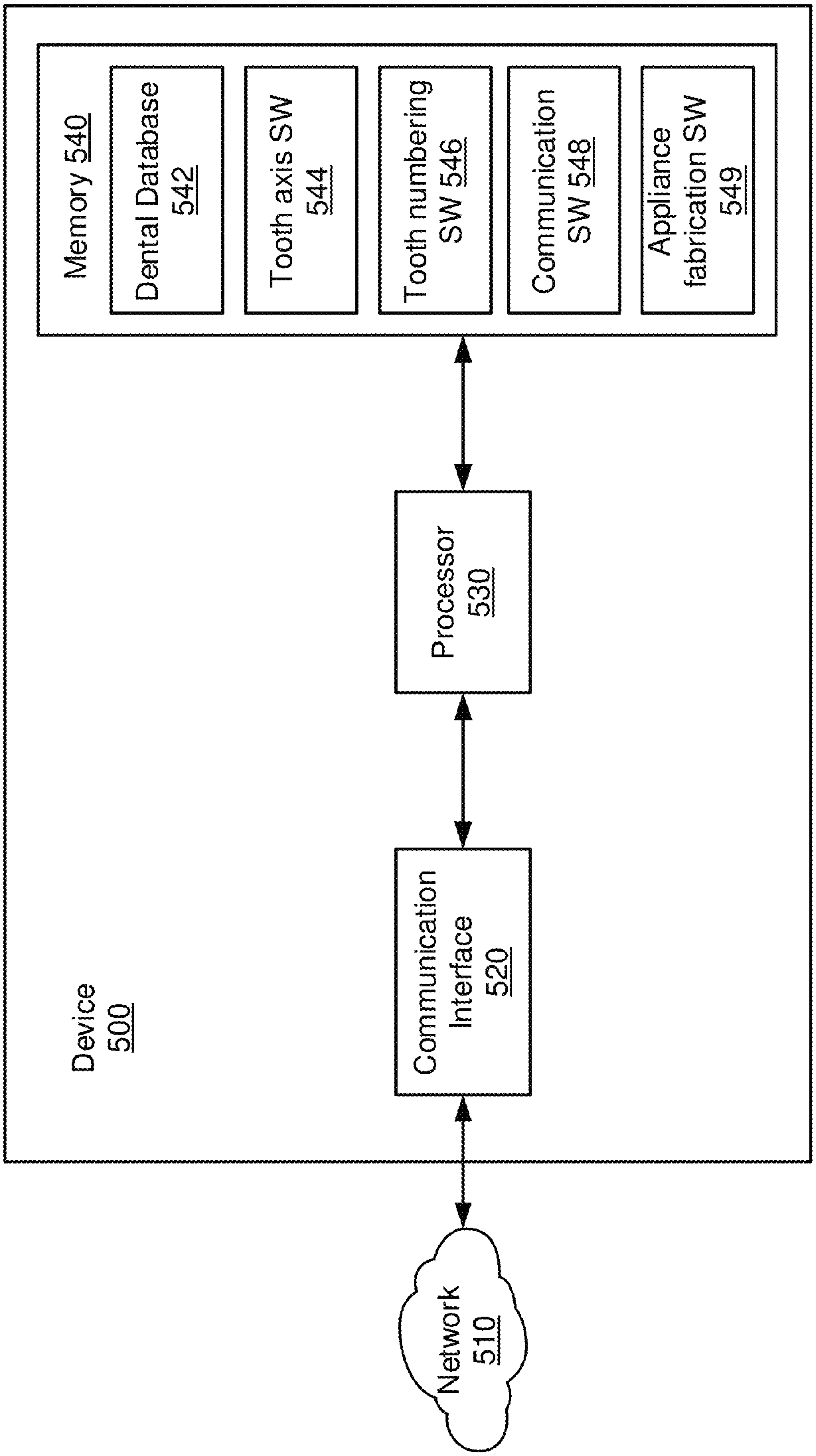
FIG. 5 is a block diagram of an apparatus that may be one example of part or all of a system as described herein.

FIG. 5 is a block diagram of a device 500 that may be one example of part or all of the system 100 of FIG. 1. Although described herein as a device, the functionality of the device 500 may be performed by any feasible apparatus, system, or method. The device 500 may include a communication interface 520, a processor 530, and a memory 540.

The communication interface 520, which may be coupled to a network (such as network 510) and to the processor 530, may transmit signals to and receive signals from other wired or wireless devices, including remote (e.g., cloud-based) storage devices, cameras, processors, compute nodes, processing nodes, computers, mobile devices (e.g., cellular phones, tablet computers and the like) and/or displays. For example, the communication interface 520 may include wired (e.g., serial, ethernet, or the like) and/or wireless (Bluetooth, Wi-Fi, cellular, or the like) transceivers that may communicate with any other feasible device through any feasible network. In some examples, the communication interface 520 may receive previous dental data and/or current dental data.

The processor 530, which is also coupled to the memory 540, may be any one or more suitable processors capable of executing scripts or instructions of one or more software programs stored in the device 500 (such as within memory 540).

The memory 540 may include a dental database 542. The dental database 542 may include a subject's previous dental data and a subject's current dental data. Dental data, as described herein, may include 2D and 3D image information, dental model information, as well as any feasible tooth information, including tooth segmentation, tooth axis, and tooth numbering information.

The memory 540 may also include a non-transitory computer-readable storage medium (e.g., one or more nonvolatile memory elements, such as EPROM, EEPROM, Flash memory, a hard drive, etc.) that may store a tooth axis (SW) module 544, a tooth numbering SW module 546, communication SW module 548, and an appliance fabrication SW module 549. Each software module includes program instructions that, when executed by the processor 530, may cause the device 500 to perform the corresponding function(s). Thus, the non-transitory computer-readable storage medium of memory 540 may include instructions for performing all or a portion of the operations described herein.

The processor 530 may execute the tooth axis SW module 544 to determine tooth axis information for teeth included in a subject's current dental data. In some examples, execution of the tooth axis SW module 544 may match teeth included in both the previous dental data and the current dental data, import tooth axis information from the previous dental data to the current dental data, and (in some cases) adjust the imported tooth axis information. Execution of the tooth axis SW module 544 may cause the processor 530 and/or the device 500 to perform one or more of the operations discussed with respect to FIGS. 1-3.

The processor 530 may execute the tooth numbering SW module 546 to determine tooth numbers for teeth included in a subject's current dental data. In some examples, execution of the tooth numbering SW module 546 may cause the processor 530 to import tooth numbering data or information from the previous dental data into the current dental data. Execution of the tooth numbering SW module 546 may cause the processor 530 and/or the device 500 to compare tooth numbering of teeth between both the previous dental data and the current dental data to identify tooth number errors within the current dental data. In some examples, execution of the tooth numbering SW module 546 may cause the processor to correct identified errors using tooth numbering data from the previous dental data. Execution of the tooth numbering SW module 546 may cause the processor 530 and/or the device 500 to perform one or more of the operations discussed with respect to FIG. 4.

The processor 530 may execute the appliance fabrication SW module 549 to generate aligner data that, in turn, may be used to fabricate one or more aligners. For example, execution of the appliance fabrication SW module 549 may use dental data (a subject's current dental data) stored in the memory 540 to generate aligner data for a series of aligners.

In general, these methods and apparatuses (systems, devices, etc., including software, hardware and/or firmware) for correcting the tooth axis and/or for determining tooth number of a dental (intraoral) scan based on a prior treatment may include any of the components described herein, as illustrated and described in FIGS. 1-5, discussed above, which may collectively be referred to as tooth axis determination and may include a tooth axis determination module, and/or tooth numbering and may include a tooth numbering module, and may be used at one or more parts of a dental computing environment, including as part of an intraoral scanning system, doctor system, treatment planning (e.g., technician) system, patient system, and/or fabrication system. In particular, these methods and apparatuses may be used as part of a treatment planning system. The tooth axis determination may, in some examples, include tooth axis setting and/or tooth axis verification and thus described herein are tooth axis setting modules and/or tooth axis verification module that may use any of these methods and techniques and may be used at one or more parts of a dental computing environment. Similarly, the tooth numbering may include or refer to tooth numbering verification and/or tooth numbering setting, and the methods and apparatuses described herein may include a tooth number verification module and/or a tooth numbering setting module, and may be used at one or more parts of a dental computing environment.

Figure 6:
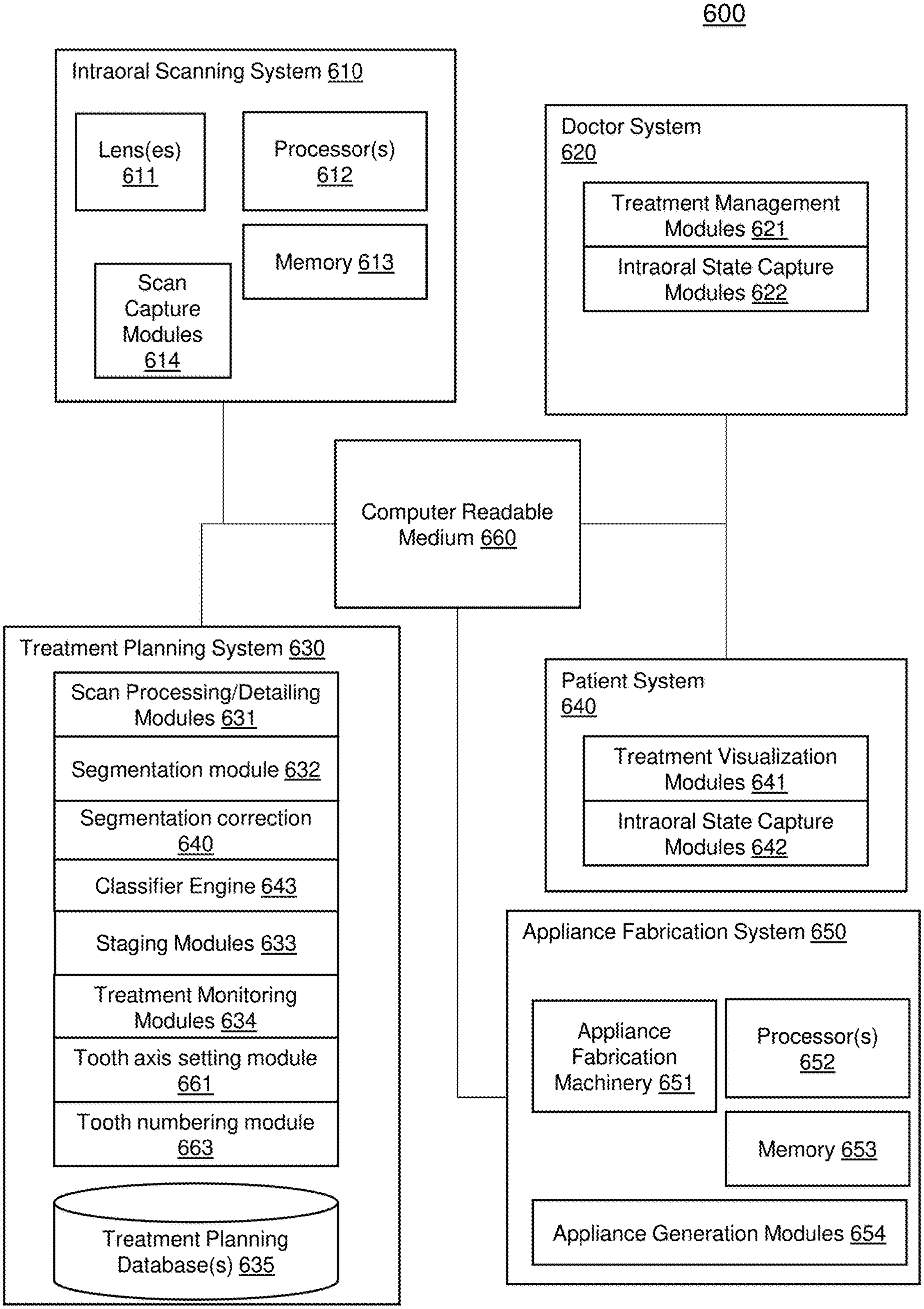
FIG. 6 shows a diagram illustrating an example of a computing environment including the segmentation correction module(s), described herein.

FIG. 6 is a diagram illustrating one variation of a computing environment 600 that may generate one or more orthodontic/dental appliances and/or treatment plans specific to a patient, and fabricate dental appliances that may accomplish the treatment plan to treat a patient, under the direction of a dental professional. The example computing environment 600 shown in FIG. 6 includes an intraoral scanning system 610, a doctor system 620, a treatment planning system 630 (e.g., technician system), a patient system 640, an appliance fabrication system 650, and computer-readable medium 60. Each of these systems may be referred to equivalently as a sub-system of the overall system (e.g., computing environment). Although shown as discrete systems, some or all of these systems may be integrated and/or combined. In some variations a computing environment (dental computing system) 600 may include just one or a subset of these systems (which may also be referred to as sub-systems of the overall system 600). As mentioned, one or more of these systems may be combined or integrated with one or more of the other systems (sub-systems), such as, e.g., the patient system and the doctor system may be part of a remote server accessible by doctor and/or patient interfaces. The computer readable medium 60 may divided between all or some of the systems (subsystems); for example, the treatment planning system and appliance fabrication system may be part of the same sub-system and may be on a computer readable medium 60. Further, each of these systems may be further divided into sub-systems or components that may be physically distributed (e.g., between local and remote processors, etc.) or may be integrated.

An intraoral scanning system may include an intraoral scanner as well as one or more processors for processing images. For example, an intraoral scanning system 610 can include optics 611 (e.g., one or more lenses, filters, mirrors, etc.), processor(s) 612, a memory 613, and a scan capture module 614. In general, the intraoral scanning system 610 can capture one or more images of a patient's dentition. Use of the intraoral scanning system 610 may be in a clinical setting (doctor's office or the like) or in a patient-selected setting (the patient's home, for example). In some cases, operations of the intraoral scanning system 610 may be performed by an intraoral scanner, dental camera, cell phone or any other feasible device.

The optical components 611 may include one or more lenses and optical sensors to capture reflected light, particularly from a patient's dentition. The scan capture module 614 can include instructions (such as non-transitory computer-readable instructions) that may be stored in the memory 613 and executed by the processor(s) 612 to can control the capture of any number of images of the patient's dentition.

In FIG. 6 the segmentation 632 and verification 632 (e.g., segmentation correction module(s) 640, classifier engine 643) are shown as part of the treatment planning sub-system 630, however in some examples some, or all, of these components may be part of (or duplicated in) the intraoral scanning system 610. For example, the segmentation module 632 may be in the intraoral scanning sub-system 610 or another sub-system and the segmentation correction module(s) 640 may be in the treatment planning sub-system 630 or some other sub-system. In some examples the classifier engine 643 may be integrated with the segmentation correction 640 module(s). Any of the component systems or sub-systems of the dental computing environment 600 may access or use the segmented data. Similarly the tooth axis setting module 661 and/or the tooth numbering module 663 may be part of the treatment planning sub-system 630, however in some examples some, or all, of these components may be part of (or duplicated in) the intraoral scanning system 610.

The doctor system 620 (e.g., doctor sub-system) may include a treatment management module 621 and an intraoral state capture module 622 that may access or use the 3D model based on the segmented data. The doctor system 620 may provide a "doctor facing" interface to the computing environment 600. The treatment management module 621 can perform any operations that enable a doctor or other clinician to manage the treatment of any patient. In some examples, the treatment management module 621 may provide a visualization and/or simulation of the patient's dentition with respect to a treatment plan. This user interface may also include display the segmentation.

The intraoral state capture module 622 can provide images of the patient's dentition to a clinician through the doctor system 620. The images may be captured through the intraoral scanning system 610 and may also include images of a simulation of tooth movement based on a treatment plan.

In some examples, the treatment management module 621 can enable the doctor to modify or revise a treatment plan, particularly when images provided by the intraoral state capture module 622 indicate that the movement of the patient's teeth may not be according to the treatment plan. The doctor system 620 may include one or more processors configured to execute any feasible non-transitory computer-readable instructions to perform any feasible operations described herein.

Alternatively or additionally, the treatment planning system 630 may include any of the methods and apparatuses described herein. The treatment planning system 630 may include scan processing/detailing module 631, segmentation module 632, segmentation correction module(s) 640, classifier engine(s) 643, staging module 633, and treatment monitoring module 634, and a treatment planning database(s) 635. In general, the treatment planning system 630 can determine a treatment plan for any feasible patient. The scan processing/detailing module 631 can receive or obtain dental scans (such as scans from the intraoral scanning system 610) and can process the scans to "clean" them by removing scan errors and, in some cases, enhancing details of the scanned image. The treatment planning system 630 may perform segmentation. For example, a treatment planning system may include a segmentation module 632 that can segment a dental model into separate parts including separate teeth, gums, jaw bones, and the like. In some cases, the dental models may be based on scan data from the scan processing/detailing module 631 and/or segmentation data from the segmentation module and segmentation correction modules 640 (and/or classifier engine 643).

The staging module 633 may determine different stages of a treatment plan. Each stage may correspond to a different dental aligner. The staging module 633 may also determine the final position of the patient's teeth, in accordance with a treatment plan. Thus, the staging module 633 can determine some or all of a patient's orthodontic treatment plan. In some examples, the staging module 633 can simulate movement of a patient's teeth in accordance with the different stages of the patient's treatment plan.

An optional treatment monitoring module 634 can monitor the progress of an orthodontic treatment plan. In some examples, the treatment monitoring module 634 can provide an analysis of progress of treatment plans to a clinician. Although not shown here, the treatment planning system 630 can include one or more processors configured to execute any feasible non-transitory computer-readable instructions to perform any feasible operations described herein.

The Tooth axis setting module 661 and/or Tooth numbering module 663 may be included as part of the treatment planning sub-system 630 as discussed above, and may include the features and perform th steps described above foe either tooth numbering/setting or verification and/or for tooth axis determination, setting and/or verification.

The patient system 640 can include a treatment visualization module 641 and an intraoral state capture module 642. In general, the patient system 640 can provide a "patient facing" interface to the computing environment 600. The treatment visualization module 641 can enable the patient to visualize how an orthodontic treatment plan has progressed and also visualize a predicted outcome (e.g., a final position of teeth).

In some examples, the patient system 640 can capture dentition scans for the treatment visualization module 641 through the intraoral state capture module 642. The intraoral state capture module can enable a patient to capture his or her own dentition through the intraoral scanning system 610. Although not shown here, the patient system 640 can include one or more processors configured to execute any feasible non-transitory computer-readable instructions to perform any feasible operations described herein.

The appliance fabrication system 650 can include appliance fabrication machinery 651, processor(s) 652, memory 653, and appliance generation module 654. In general, the appliance fabrication system 650 can directly or indirectly fabricate aligners to implement an orthodontic treatment plan. In some examples, the orthodontic treatment plan may be stored in the treatment planning database(s) 635. Any of these apparatuses and methods may be configured to include the step of fabricating one or more (e.g., a series) of dental appliances using a 3D model (e.g., including using the corrected segmentation, as described herein).

The appliance fabrication machinery 651 may include any feasible implement or apparatus that can fabricate any suitable dental aligner. The appliance generation module 654 may include any non-transitory computer-readable instructions that, when executed by the processor(s) 652, can direct the appliance fabrication machinery 651 to produce one or more dental aligners. The memory 653 may store data or instructions for use by the processor(s) 652. In some examples, the memory 653 may temporarily store a treatment plan, dental models, or intraoral scans.

The computer-readable medium 60 may include some or all of the elements described herein with respect to the computing environment 600. The computer-readable medium 60 may include non-transitory computer-readable instructions that, when executed by a processor, can provide the functionality of any device, machine, or module described herein.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being “directly connected”, “directly attached” or “directly coupled” to another feature or element, there are no intervening features or elements present. Although described or shown with respect to one embodiment, the features and elements so described or shown can apply to other embodiments. It will also be appreciated by those of skill in the art that references to a structure or feature that is disposed “adjacent” another feature may have portions that overlap or underlie the adjacent feature.

The terminology used herein is for the purpose of describing particular embodiments only and is not intended to be limiting of the invention. For example, as used herein, the singular forms “a”, “an” and “the” are intended to include the plural forms as well, unless the context clearly indicates otherwise. It will be further understood that the terms “comprises” and/or “comprising,” when used in this specification, specify the presence of stated features, steps, operations, elements, and/or components, but do not preclude the presence or addition of one or more other features, steps, operations, elements, components, and/or groups thereof. As used herein, the term “and/or” includes any and all combinations of one or more of the associated listed items and may be abbreviated as “/”.

Spatially relative terms, such as “under”, “below”, “lower”, “over”, “upper” and the like, may be used herein for ease of description to describe one element or feature’s relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as “under” or “beneath” other elements or features would then be oriented “over” the other elements or features. Thus, the exemplary term “under” can encompass both an orientation of over and under. The device may be otherwise oriented (rotated 90 degrees or at other orientations) and the spatially relative descriptors used herein interpreted accordingly. Similarly, the terms “upwardly”, “downwardly”, “vertical”, “horizontal” and the like are used herein for the purpose of explanation only unless specifically indicated otherwise.

Although the terms “first” and “second” may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word “comprise”, and variations such as “comprises” and “comprising” means various components can be co-jointly employed in the methods and articles (e.g., compositions and apparatuses including device and methods). For example, the term “comprising” will be understood to imply the inclusion of any stated elements or steps but not the exclusion of any other elements or steps.

In general, any of the apparatuses and/or methods described herein should be understood to be inclusive, but all or a sub-set of the components and/or steps may alternatively be exclusive, and may be expressed as “consisting of” or alternatively “consisting essentially of” the various components, steps, sub-components or sub-steps.

As used herein in the specification and claims, including as used in the examples and unless otherwise expressly specified, all numbers may be read as if prefaced by the word “about” or “approximately,” even if the term does not expressly appear. The phrase “about” or “approximately” may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value “10” is disclosed, then “about 10” is also disclosed. Any numerical range recited herein is intended to include all sub-ranges subsumed therein. It is also understood that when a value is disclosed that “less than or equal to” the value, “greater than or equal to the value” and possible ranges between values are also disclosed, as appropriately understood by the skilled artisan. For example, if the value “X” is disclosed the “less than or equal to X” as well as “greater than or equal to X” (e.g., where X is a numerical value) is also disclosed. It is also understood that the throughout the application, data is provided in a number of different formats, and that this data, represents endpoints and starting points, and ranges for any combination of the data points. For example, if a particular data point “10” and a particular data point “15” are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the individual matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term “invention” merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method, the method comprising:

identifying a best match of a digital model of a subject's current dentition to a digital model of the subject's prior dentition, wherein the prior dentition corresponds to a previous dental or orthodontic treatment comprising a plurality of treatment stages, wherein identifying the best match comprises:

matching a plurality of teeth positions of the subject's current dentition for the plurality of treatment stages to determine a best matching treatment stage of the plurality of treatment stages of the previous dental or orthodontic treatment; and importing tooth axis information from the best matching treatment stage for teeth of the digital model of the subject's current dentition when deviations between tooth shapes of the subject's current dentition and tooth shapes of the best matching treatment stage are below a threshold;

revising the digital model of the subject's current dentition; and fabricating a dental appliance based on a revised digital model.

2. The method of claim 1, wherein identifying the best match comprises matching a jaw position of the digital model of the subject's current dentition to a jaw position of the digital model of the subject's prior dentition prior to matching the plurality of teeth positions of the subject's current dentition for the plurality of treatment stages.

3. The method of claim 1, wherein importing the tooth axis information from the best matching treatment stage comprises setting a position of a tooth axis for individual teeth of the digital model of the subject's current dentition wherein the position of each tooth axis is transformed based on a comparison of the tooth shapes between the subject's current dentition and the best matching treatment stage.

4. The method of claim 1, further comprising receiving the digital model of the subject's current dentition.

5. The method of claim 1, further comprising receiving the digital model of the subject's prior dentition.

6. The method of claim 1, wherein the digital model of the subject's current dentition is segmented to identify individual teeth.

7. The method of claim 1, wherein tooth axis information for each tooth includes distinct tooth axis information for each individual tooth.

8. The method of claim 1, further comprising outputting the revised digital model of the subject's current dentition for generating a new orthodontic treatment plan.

9. The method of claim 1, wherein the digital model of the subject's current dentition is received from an intraoral scanner.

10. The method of claim 1, wherein the tooth axis information includes at least one of a polar and cartesian axes.

11. The method of claim 1, wherein matching teeth is performed on a remote server.

12. The method of claim 1, further comprising setting tooth numbering for at least some of the teeth of the digital model of the subject's current dentition based on tooth number of teeth of the best matching treatment stage when the deviations between tooth shapes of the subject's current dentition and tooth shapes of the best matching treatment stage are below the threshold.

13. A method, the method comprising:

receiving a digital model of a subject's current dentition;

receiving a digital model of the subject's prior dentition, wherein the prior dentition corresponds to a previous dental or orthodontic treatment comprising a plurality of treatment stages;

identifying a best match of the digital model of the subject's current dentition to the digital model of the subject's prior dentition, wherein identifying the best match comprises:

matching a jaw position of the digital model of the subject's current dentition to a jaw position of the digital model of the subject's prior dentition; and matching a plurality of teeth positions of the subject's current dentition for the plurality of treatment stages to determine a best matching treatment stage of the plurality of treatment stages of the previous dental or orthodontic treatment; and importing tooth axis information from the best matching treatment stage for teeth of the digital model of the subject's current dentition when deviations between tooth shapes of the subject's current dentition and tooth shapes of the best matching treatment stage are below a threshold;

outputting a revised digital model of the subject's current dentition for generating a new orthodontic treatment plan; and fabricating a dental appliance based on the revised digital model.

14. A non-transitory computer-readable storage medium storing instructions that, when executed by one or more processors, cause the one or more processors to perform a method comprising:

identifying a best match of a digital model of a subject's current dentition to a digital model of the subject's prior dentition, wherein the prior dentition corresponds to a previous dental or orthodontic treatment comprising a plurality of treatment stages, wherein identifying the best match comprises:

matching a plurality of teeth positions of the subject's current dentition for the plurality of treatment stages to determine a best matching treatment stage of the plurality of treatment stages of the previous dental or orthodontic treatment; and importing tooth axis information from the best matching treatment stage for teeth of the digital model of the subject's current dentition when deviations between tooth shapes of the subject's current dentition and tooth shapes of the best matching treatment stage are below a threshold; and outputting a revised digital model of the subject's current dentition for generating a new orthodontic treatment plan.

15. The non-transitory computer-readable storage medium of claim 14, wherein identifying the best match comprises matching a jaw position of the digital model of the subject's current dentition to a jaw position of the digital model of the subject's prior dentition prior to matching the plurality of teeth positions of the subject's current dentition for the plurality of treatment stages.

16. The non-transitory computer-readable storage medium of claim 14, wherein importing the tooth axis information from the best matching treatment stage comprises setting a position of a tooth axis for individual teeth of the digital model of the subject's current dentition wherein the position of each tooth axis is transformed based on a comparison of the tooth shapes between the subject's current dentition and the best matching treatment stage.

17. The non-transitory computer-readable storage medium of claim 14, further comprising receiving the digital model of the subject's current dentition.

18. The non-transitory computer-readable storage medium of claim 14, further comprising receiving the digital model of the subject's prior dentition.

19. The non-transitory computer-readable storage medium of claim 14, wherein the digital model of the subject's current dentition is segmented to identify individual teeth.

20. The non-transitory computer-readable storage medium of claim 14, wherein tooth axis information for each tooth includes distinct tooth axis information for each individual tooth.

21. The non-transitory computer-readable storage medium of claim 14, further comprising outputting the revised digital model of the subject's current dentition for generating the new orthodontic treatment plan.

22. The non-transitory computer-readable storage medium of claim 14, wherein the digital model of the subject's current dentition is received from an intraoral scanner.

23. The non-transitory computer-readable storage medium of claim 14, wherein the tooth axis information includes at least one of a polar and cartesian axes.

24. The non-transitory computer-readable storage medium of claim 14, wherein matching teeth is performed on a remote server.

* * * * *